United States Patent [19]

Toda et al.

[11] Patent Number: 4,644,021

[45] Date of Patent: Feb. 17, 1987

[54] SUSTAINED RELEASE ANTIMICROBIAL AGENTS AND METHODS OF FOULING CONTROL USING THE SAME

[75] Inventors: Fumio Toda, Ehime; Masaru Okamoto, Yamato; Fujiaki Mochizuki, Atsugi, all of Japan

[73] Assignee: Kurita Water Industries Ltd., Tokyo, Japan

[21] Appl. No.: 766,845

[22] Filed: Aug. 16, 1985

[30] Foreign Application Priority Data

Aug. 21, 1984 [JP] Japan .................. 59-173771

[51] Int. Cl.$^4$ .......................... C09D 5/14; C02F 1/68
[52] U.S. Cl. ................... 523/122; 106/15.05; 106/18.32; 106/18.33; 210/764; 424/14; 514/359; 514/772
[58] Field of Search ............... 106/15.05, 18.32, 18.33; 523/122; 210/764; 424/14; 514/772, 359

[56] References Cited

U.S. PATENT DOCUMENTS

| | | | |
|---|---|---|---|
| 4,086,297 | 4/1978 | Rei et al. | 523/122 |
| 4,115,130 | 9/1978 | Crump et al. | 106/18.33 |
| 4,243,403 | 1/1981 | Lewis et al. | 523/122 |
| 4,505,889 | 3/1985 | Amick | 210/764 |
| 4,569,989 | 2/1986 | Madison | 523/122 |

FOREIGN PATENT DOCUMENTS 57-207657 12/1982 Japan .................. 523/122

*Primary Examiner*—Ronald W. Griffin
*Attorney, Agent, or Firm*—Frank J. Jordan; C. Bruce Hamburg; Manabu Kanesaka

[57] ABSTRACT

Sustained release antimicrobial agents comprising a clathrate compound composed of a water-soluble antimicrobial agent, and 1,1,6,6-tetraphenyl-2,4-hexadiyne-1,6-diol or 1,1-di(2,4-dimethylphenyl)-2-propyne-1-ol, and methods of fouling control using the same.

12 Claims, No Drawings

SUSTAINED RELEASE ANTIMICROBIAL AGENTS AND METHODS OF FOULING CONTROL USING THE SAME

FIELD OF THE INVENTION AND RELATED ART STATEMENT

This invention relates to sustained release antimicrobial agents and methods of fouling control using the same. More particularly, it relates to sustained release antimicrobial agents capable of maintaining their antimicrobial activity over long periods and to methods of fouling control using the same.

In the water systems of the paper and pulp industry, cooling-water systems in industrial facilities and in many other water systems, slime of animal, plant and microbial origin tend to deposit, often causing various hazards.

In general cooling-water systems, deposition of slime of zoogloea, algae and filamentous fungi, reduces thermal efficiency, adversely affects circulation of water, and induces corrosion of metal parts.

In the paper and pulp industry, slime of bacteria, filamentous fungi and yeast occurs mainly in the paper mill process. This enters pulp slurry as impurities, degrading the quality of final products, often leading to paper breakage to greatly reduce production efficiency, and causing many other troubles. Use of recirculated water is increasing in recent years, and this makes slime control an issue of greater importance.

In thermoelectric power plants and ironworks that employ seawater, marine algae and bacteria, mytilus, protochordata and other living matters deposit at seawater intakes and on the internal surfaces of cooling pipes, thus lowering water-intake and cooling efficiency. These deposits are also detached and carried by flowing water and often clog other parts of facility, such as tubes of heat exchangers and strainers, retarding flow of water and degrading the performances of the entire system.

To prevent such troubles caused by deposition of slime, microorganisms, shellfishes, etc., it is customary to use antimicrobial agents (slime control agents) because of low cost and easy treatment. The most popularly used are water-soluble slime control agents, such as hydrazine ($N_2H_4$) and isothiazoline compounds. Of these, 5-chloro-2-methyl-4-isothiazolin-3-one (hereinafter abbreviated as "CMI") represented by formula (I) given below has exceptionally high antimicrobial activity and is extensively used as slime controller, bactericide, algicide and fungicide in cooling-water systems, paper and pulp industry, swimming pools and other water systems.

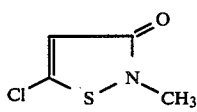

(I)

CMI is produced (1) by halogenation of β-thioketoamide in an inert organic ester such as ethyl acetate, or (2) by treatment of a β-substituted thiocyanoacrylamide or thiosulfatoacrylamide with an acid to give isothiazolone, followed by halogenation [Japanese Patent Publication No. 21240 (1971)]. It is commercially available from Rohm & Hass under the trade name of KATHON 886.

Either one of the two processes mentioned above, (1) and (2), fails to selectively give CMI, but affords mixtures containing, as impurities, 2-methyl-4-isothiazolin-3-one (hereinafter abbreviated as "MI")represented by formula (II) shown below—a substance having lower antimicrobial activity than CMI by a factor of 10—and inorganic salts, such as magnesium chloride and nitrate, which have no antimicrobial activity at all.

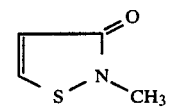

(II)

It is impracticable to isolate CMI from the reaction mixture; hence, CMI is employed in impure form containing MI and other impurities. In fact, KATHON 886 is composed of 8.5% CMI, 2.5% MI, 9% magnesium chloride, 16% magnesium nitrate and 64% water.

KATHON 886 is a product showing considerably high antimicrobial activity, but has some problems at the same time. It is highly irritant to the skin, requiring extra care in handling. It tends to react with some organic substances in water (amines, reducing matters, etc.) with the consequent loss of its activity, making it difficult to maintain its action over long periods. When formulated in antifouling paint for use in water, it readily comes out of the applied paint layer into water phase and hence the antifouling effect does not last over long periods.

Hydrazine (containing 60% water) also suffers from the following problems: (1) it is a reducing, alkaline liquid having irritating action to the skin; (2) safety standard stipulates that the concentration of hydrazine be kept below 1 ppm, requiring careful control in actual operation; (3) hydrazine reacts with oxygen in water by the action of catalyst, such as copper ions, rapidly decomposing and losing its activity, and hence it is difficult to maintain the antimicrobial activity over long periods; and (4) similar to CMI, its effect does not last for long periods when formulated in antifouling paint for use in water.

As stated above, the water-soluble antimicrobial agents commonly used at present are very unsatisfactory in terms of handling and antimicrobial effect because of their toxicity, high solubility in water, and tendency of rapidly losing activity.

OBJECT AND SUMMARY OF THE INVENTION

The primary object of this invention is to provide sustained release antimicrobial agents with high antimicrobial activity and methods of fouling control using the same, which are free from the problems described above.

A further object of this invention is to provide sustained release antimicrobial agents capable of maintaining the antimicrobial activity over long periods, and methods of fouling control using the same.

Another object of this invention is to provide sustained release antimicrobial agents which are low in toxicity and are easy to handle, and methods of fouling control using the same.

These objects can be achieved by a sustained release antimicrobial agent comprising a clathrate compound composed of a water-soluble antimicrobial agent, and 1,1,6,6-tetraphenyl-2,4-hexadiyne-1,6-diol or 1,1-di(2,4-dimethylphenyl)-2-propyne-1-ol, and by a process for fouling control which comprises treatment with a clathrate compound composed of a water-soluble antimicrobial agent, and 1,1,6,6-tetraphenyl-2,4-hexadiyne-1,6-diol or 1,1-di(2,4-dimethylphenyl)-2-propyne-1-ol.

DETAILED DESCRIPTION OF PREFERRED EMBODIMENTS

The water-soluble antimicrobial agent used in this invention may be any water-soluble antimicrobial agent that can form a clathrate compound together with 1,1,6,6-tetraphenyl-2,4-hexadiyne-1,6-diol (hereinafter abbreviated as ("TPH") or 1,1-di(2,4-dimethylphenyl)-2-propyne-1-ol (hereinafter abbreviated as "DMP"). Hydrazine and CMI, which are widely used as effective antimicrobial agent, are typical examples, but other compounds, such as bromonitroalcohols, dithiol-3-one, 2,2-dibromo-3-nitropropionamide, thiocyanates and their derivatives, may also be used.

TPH and DMP are compounds represented by formulas (III) and (IV), respectively.

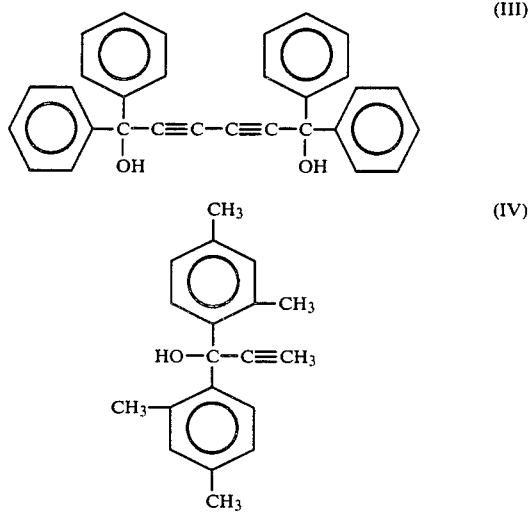

The clathrate compounds of this invention can be prepared from the materials shown below, (a), (b) and (c).
  (a) A solution of TPH or DMP in a water-soluble solvent (e.g., methanol and ethanol)
  (b) A water-soluble antimicrobial agent, such as CMI and hydrazine
  (c) A mixture of water-soluble antimicrobial agent and other impurities Slow addition of (a) and (b), or (a) and (c), into water gives a corresponding clathrate compound as precipitate, which can be separated by usual method (e.g., collection on filter paper by filtration).

This preparative method is advanageous in that, even when a water-soluble antimicrobial agent containing much impurities is used as starting material, only the effective component contained in it is selectively included in the resulting clathrate compound.

The water-soluble antimicrobial agent (e.g., CMI and hydrazine) is selectively included as guest molecule in TPH or DMP (host molecule), and separates out in the form of a clathrate compound. The reaction normally proceeds according to the schemes shown below, although there may be slight changes depending on reaction conditions.

$$TPH + 2CMI \rightarrow TPH (CMI)_2$$

$$2DMP + CMI \rightarrow (DMP)_2 CMI$$

$$TPH + 2N_2H_4 \cdot H_2O \rightarrow TPH (N_2H_4 \cdot H_2O)_2$$

The clathrate compounds of this invention thus obtained are powdery solid, and can be easily fabricated into any desired form (e.g., tablets). Since the antimicrobial agent is included in the host molecule in the form of clathrate compound, toxicity is low and handling is also very easy.

The sustained release antimicrobial agents of this invention may contain, other than a clathrate compound as defined above, binder, solvent, carrier, humectant, filler and other additives, as required. The preferable content of clathrate compound is not smaller than 1 wt %, more preferably in the range of 5 to 50 wt %.

The process for slime control of this invention comprises treating water or equipment surfaces with a sustained release antimicrobial agent of this invention containing a clathrate compound as defined above. Preferred embodiments of such treatment include the following:

(1) The water being treated is allowed to flow through a column packed with a sustained release antimicrobial agent of this invention.

(2) The agent of this invention is charged in bags or cartridges that are insoluble in water but are permeable to water, and the bags or cartridges are set submerged or afloat in the water system being treated.

(3) The agent of this invention, powdery or shaped, is allowed to flow in the water system being treated in the form of dispersion.

(4) The agent of this invention is admixed to a resin coating or the like, which is coated on the surfaces of equipment used in the water system.

(5) The agent of this invention is fixed to the surfaces of objects being protected by a suitable means (e.g., bonding with an adhesive).

As may be apparent from the foregoing, the sustained release antimicrobial agents of this invention comprise a clathrate compound composed of a watrer-soluble antimicrobial agent (effective component) and TPH or DMP, and therefore have the following advantages:

(1) Since the effective component gradually comes into solution, the antimicrobial activity lasts over very long periods.

(2) Can be fabricated into any desired shape (e.g., tablets) for ease of handling.

(3) Higher safety and better working environment because of lowered toxicity and reduced irritative action to the skin as a result of inclusion in the form of clathrate compound.

(4) No tendency of losing antimicrobial activity due to reaction of the effective component with other substances.

The methods of fouling control of this invention which comprises treatment with a clathrate compound having such outstanding characteristics effectively prevents deposition of slime, microorganisms and shellfishes by a simple operation, thus completely eliminating various troubles caused by such deposits.

The following Examples further illustrate this invention but are not intended to limit its scope; any changes or modifications may be made within the spirit of this invention.

(EXAMPLE 1)

Preparation of TPH.(CMI)$_2$

To a solution of TPH (500 mg, $1.21 \times 10^{-3}$ mole) in 10 ml methanol was added 4.26 g of KATHON 886 (326 mg, $2.42 \times 10^{-3}$ mole, as CMI) with stirring, the turbid reaction mixture was allowed to stand at room temperature for three hours, and the precipitate which separated out was collected on filter paper by filtration.

NMR analysis revealed that this consists of TPH and CMI at a molar ratio of 1:2 and at a weight ratio of 58.1:41.9. It was also demonstrated by elemental analysis that this contains no MI, magnesium chloride and magnesium nitrate.

Preparation of (DMP)$_2$ CMI

To a solution of DMP (500 mg, $1.89 \times 10^{-3}$) in 10 ml methanol was added 3.32 g of KATHON 886 (283 mg, $1.89 \times 10^{-3}$ mole, as CMI) with stirring, and the reaction mixture was worked up in the same manner as above.

NMR analysis revealed that the precipitate collected consists of TPH and CMI at a molar ratio of 2:1 and at a weight ratio of 77.9:22.1. No MI, magnesium chloride nor magnesium nitrate was contained in this case, too.

CMI Dissolution Test

Samples of (1) TPH (CMI)$_2$, (2) (DMP)$_2$ CMI and (3) CMI were each placed in a 0.8 membrane filter bag (0.1 g as CMI), each bag was immersed in 1 liter of pure water under stirring, and the CMI concentration in water was measured at definite intervals. The result is summarized in Table 1.

TABLE 1

| | Changes of CMI Concentration with Time | | | | | |
| --- | --- | --- | --- | --- | --- | --- |
| | Unit: ppm | | | | | |
| Time Elapsed | 10 min | 2 hr | 4 hr | 24 hr | 48 hr | 72 hr |
| (1) | 7 | 78 | 89 | 100 | 100 | 100 |
| (2) | 0 | 18 | 20 | 28 | 55 | 67 |
| (3) | 100 | 100 | 100 | 100 | 100 | 100 |

As can be seen from Table 1, CMI, when used alone, rapidly came into solution upon immersion of the filter bag in water. With clathrate compounds, (1) and (2), on the other hand, CMI was released very gradually, indicating that the sustained release antimicrobial agents of this invention are capable of maintaining the antimicrobial activity over long periods.

(EXAMPLE 2)

A clathrate compound prepared from TPH and hydrazine hydrate (1:2 molar ratio)—sample (1)—and hydrazine hydrate (water content: 60%)—sample (2)—were each placed in a 0.8μ membrane filter bag (0.1 g as hydrazine), and the changes of hydrazine concentration was followed in the same manner as in Example 1. The result is summarized in Table 2.

TABLE 2

| | Changes of Hydrazine Concentration with Time | | | | |
| --- | --- | --- | --- | --- | --- |
| | Unit: ppm | | | | |
| Time Elapsed | 10 min | 1 hr | 2 hr | 4 hr | 24 hr |
| (1) | 4 | 40 | 72 | 87 | 100 |
| (2) | 100 | 100 | 100 | 100 | 100 |

The outstandinbg effect of the sustained release antimicrobial agent of this invention is apparent from the table.

What is claimed is:

1. A sustained release antimicrobial agent comprising a clathrate compound composed of a water-soluble antimicrobial agent, and 1,1,6,6-tetraphenyl-2,4-hexadiyne-1,6-diol or 1,1-di(2,4-dimethylphenyl)-2-propyne-1-ol.

2. The sustained release antimicrobial agent as defined in claim 1, wherein said water-soluble antimicrobial agent is 5-chloro-2-methyl-4-isothiazolin-3-one.

3. The sustained release antimicrobial agent as defined in claim 1, wherein said water-soluble antimicrobial agent is hydrazine.

4. The sustained release antimicrobial agent as defined in claim 1, wherein said clathrate compound is contained in an amount of 1 to 100 weight %.

5. The sustained release antimicrobial agent as defined in claim 1, wherein said clathrate compound is contained in an amount of 5 to 50 weight %.

6. The sustained release antimicrobial agent as defined in claim 1, wherein said clathrate compound is in the form of tablets.

7. A method of fouling control which comprises treatment with a clathrate compound composed of a water-soluble antimicrobial agent, and 1,1,6,6-tetraphenyl-2,4-hexadiyne-1,6-diol or 1,1-di(2,4-dimethylphenyl)-2-propyne-1- ol.

8. The method of fouling control as defined in claim 7, wherein water being treated is allowed to flow through a column packed with said clathrate compound.

9. The method of fouling control as defined in claim 7, wherein containers made of a material insoluble in water and permeable to water, and packed with said clathrate compound, are set submerged or afloat in the water system being treated.

10. The method of fouling control as defined in claim 7, wherein said clathrate compound is dispersed, in powder or fabricated form, in the water system being treated.

11. The method of fouling control as defined in claim 7, wherein said clathrate compound is fixed, in powder or fabricated form, to the surfaces of equipment used in the water system being treated.

12. The method of fouling control as defined in claim 7, wherein said clathrate compound is admixed to a coating resin and the composition thus obtained is coated on the surfaces of equipment used in the water system being treated.

* * * * *